(12) United States Patent
Biagtan et al.

(10) Patent No.: US 6,451,026 B1
(45) Date of Patent: Sep. 17, 2002

(54) DOCK EXCHANGE SYSTEM FOR COMPOSITE GUIDEWIRES

(75) Inventors: Emmanuel C. Biagtan; Shruti Bajaj, both of Temecula; Wayne E. Cornish, Fallbrook; Brandon Gosiengfiao, Temecula; Mark Richardson, Escondido; Peter J. D'Aquanni, San Luis Obispo, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/736,854

(22) Filed: Dec. 13, 2000

Related U.S. Application Data

(63) Continuation-in-part of application No. 09/468,976, filed on Dec. 21, 1999.

(51) Int. Cl.$^7$ ................................................. A61B 5/00
(52) U.S. Cl. ........................................ 606/108; 600/585
(58) Field of Search ..................... 600/585; 606/108; 604/528, 529, 530, 538, 539

(56) References Cited

U.S. PATENT DOCUMENTS

| | | | |
|---|---|---|---|
| 4,922,923 A | * 5/1990 | Gambale et al. | 600/585 |
| 5,117,838 A | * 6/1992 | Palmer et al. | 600/585 |
| 5,213,111 A | * 5/1993 | Cook et al. | 600/585 |
| 5,251,640 A | 10/1993 | Osborne | 128/772 |
| 5,451,209 A | 9/1995 | Ainsworth et al. | 604/96 |
| 5,464,023 A | * 11/1995 | Viera | 600/585 |
| 5,701,911 A | 12/1997 | Sasamine et al. | 128/772 |
| 5,749,837 A | 5/1998 | Palermo et al. | 600/585 |
| 5,769,796 A | 6/1998 | Palermo et al. | 600/585 |
| 5,772,609 A | 6/1998 | Nguyen et al. | 600/585 |
| 5,813,996 A | * 9/1998 | St. Germain et al. | 600/585 |
| 5,827,201 A | 10/1998 | Samson et al. | 600/585 |
| 5,951,494 A | 9/1999 | Wang et al. | 600/585 |
| 6,001,068 A | * 12/1999 | Uchino et al. | 600/585 |
| 6,019,736 A | 2/2000 | Avellanet et al. | 600/585 |
| 6,139,510 A | 10/2000 | Palermo | 600/585 |
| 6,165,140 A | 12/2000 | Ferrera | 600/585 |
| 6,186,978 B1 | 2/2001 | Samson et al. | 604/96.01 |
| 6,203,568 B1 | 3/2001 | Lombardi et al. | 623/1.13 |

FOREIGN PATENT DOCUMENTS

EP    0 744 186 B1    11/1998

* cited by examiner

Primary Examiner—David O. Reip
Assistant Examiner—Julian W. Woo
(74) Attorney, Agent, or Firm—Fulwider Patton Lee & Utecht, LLP

(57) ABSTRACT

An elongate intracorporeal guiding device for providing access to desired sites within a patients body. The device, which may be configured as a guidewire, is constructed so as to be compatible with sensitive imaging methods such as MRI and the like and not create imaging artifacts or interference with such imaging methods. The guiding device may be constructed so as to have a distal working section that has minimal metallic content or minimal content of materials that can cause imaging artifacts or interference with MRI imaging, other sensitive imaging methods or the like. The device may also have a dock exchange system to allow attachment and detachment of an extension guidewire.

14 Claims, 7 Drawing Sheets

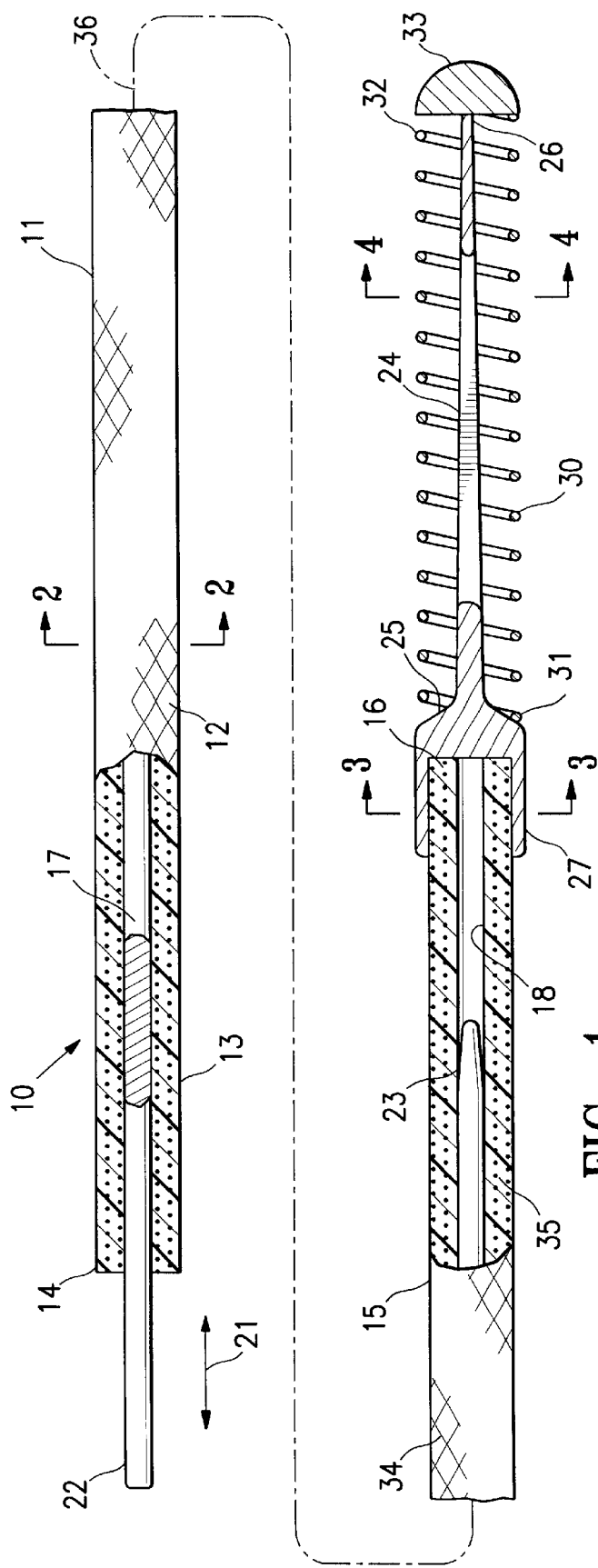

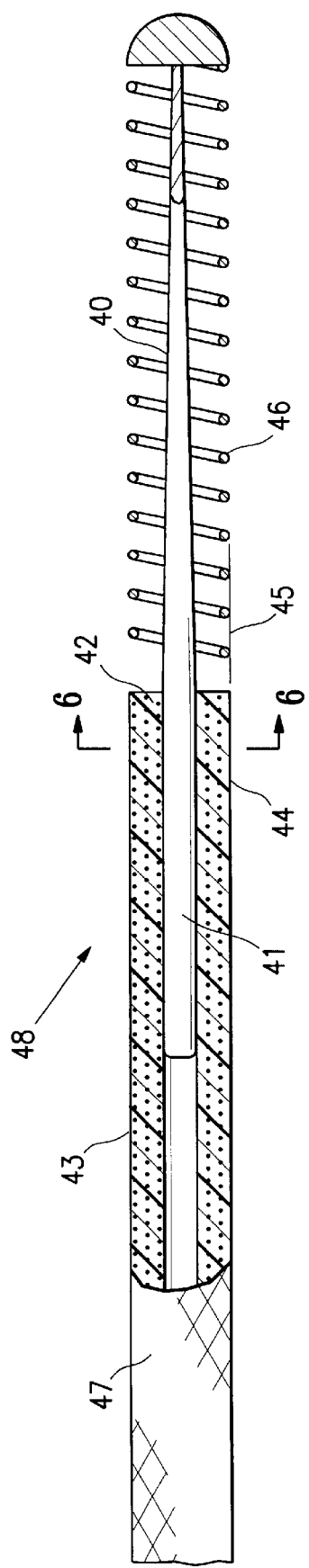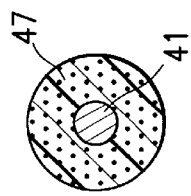
FIG. 5
FIG. 6

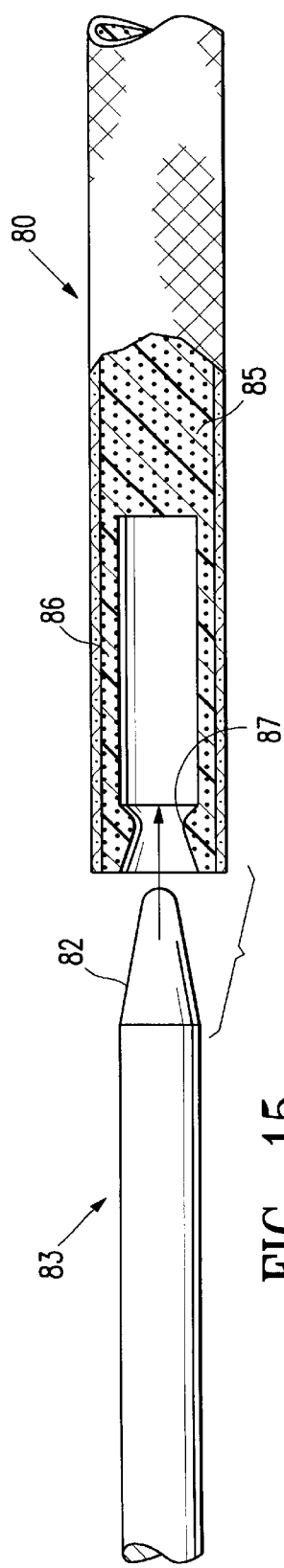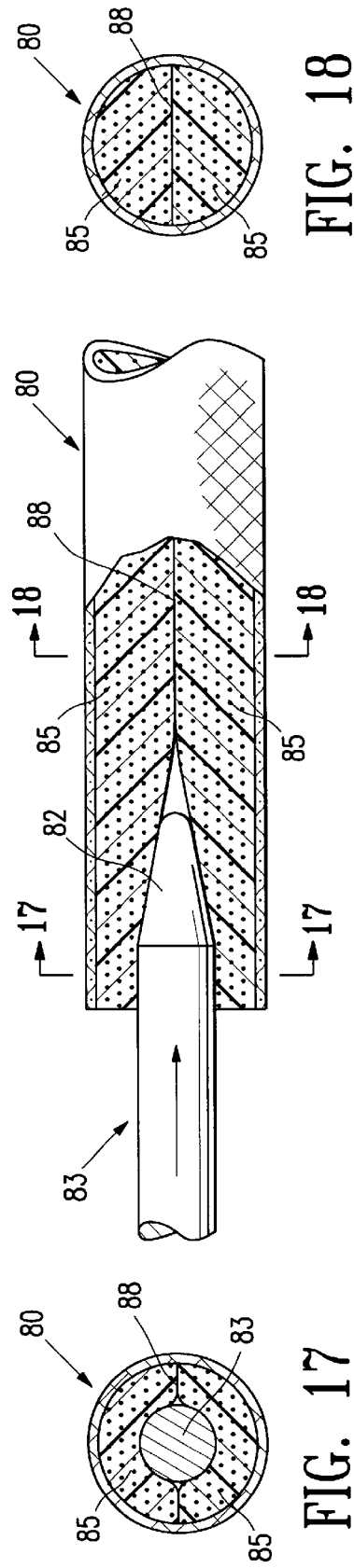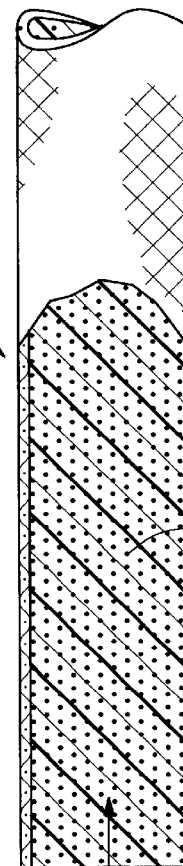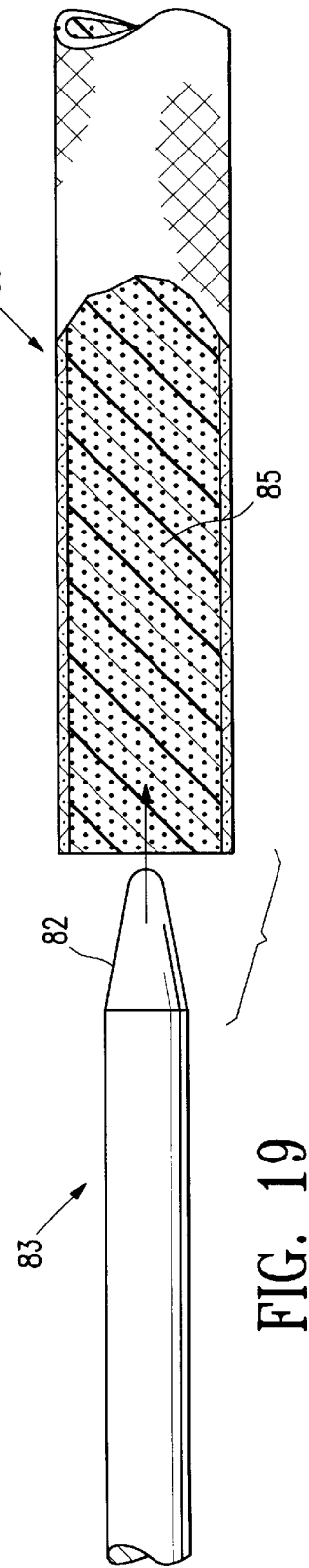

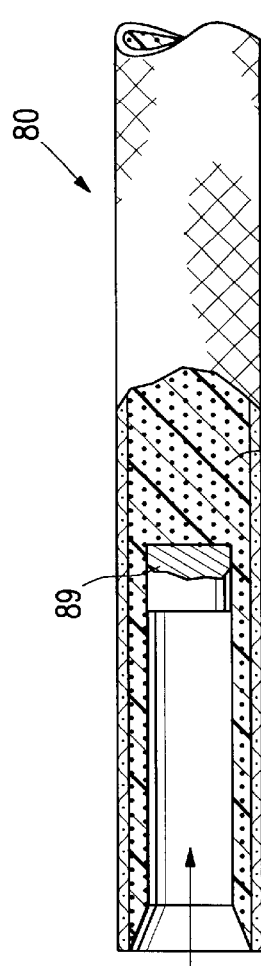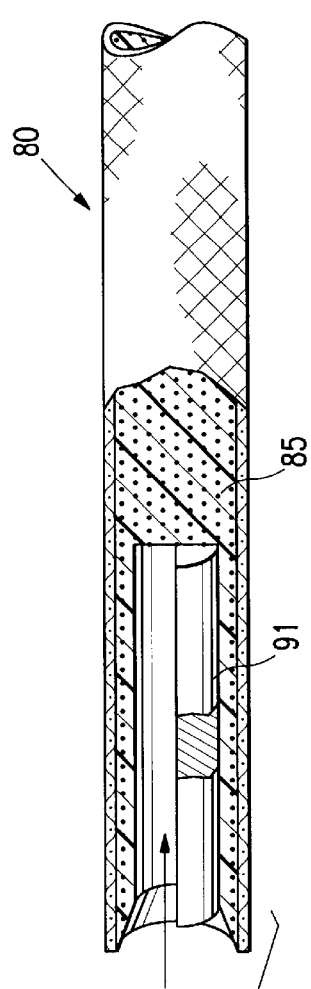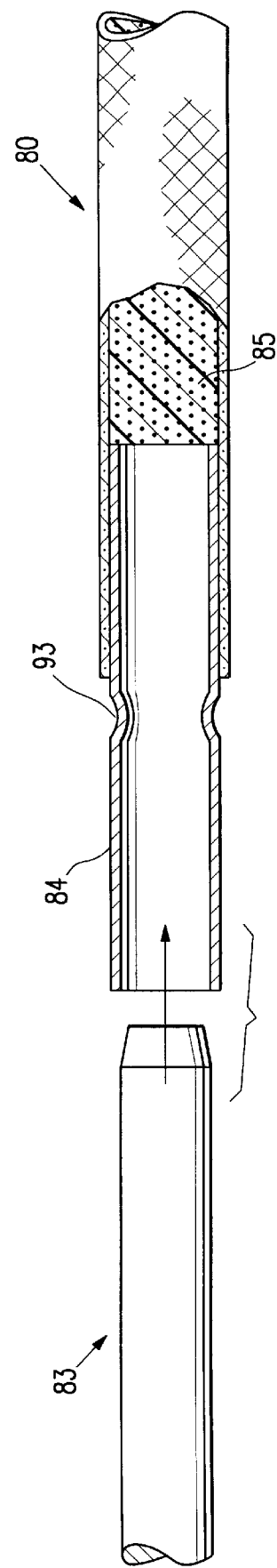

DOCK EXCHANGE SYSTEM FOR COMPOSITE GUIDEWIRES

RELATED APPLICATION

This application is a continuation-in-part of U.S. Ser. No. 09/468,976 filed on Dec. 21, 1999, which is incorporated herein in its entirety by reference.

BACKGROUND

This invention relates to the field of guidewires for advancing intraluminal devices such as stent delivery catheters, balloon dilatation catheters, atherectomy catheters and the like within a patient's body, specifically, within a patient's vasculature.

In a typical percutaneous procedure in a patient's coronary system, a guiding catheter having a preformed distal tip is percutaneously introduced into a patient's peripheral artery, e.g., femoral, radial or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the bare wire technique which is used primarily for rail type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g., a lesion to be dilated or a dilated region where a stent is to be deployed.

The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location if it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is realtached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,273 (Yock) and the previously discussed McInnes et al. which are incorporated herein by reference, is mounted onto the proximal portion of the guidewire which extends out of the proximal end of the guiding catheter which is outside of the patient. The catheter is advanced over the guidewire, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise metallic elongated core member with one or more tapered sections near the distal end thereof and a flexible body such as a metallic helical coil or a tubular body of polymeric material disposed about the distal portion of the core member. A shapable member, which may be the distal extremity of the core member or a separate shaping ribbon which is secured to the distal extremity of the core member, extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.) and U.S. Pat. No. 5,636,641 (Fariabi) which are hereby incorporated herein in their entirety by reference thereto.

Conventional metallic guidewires using tapered distal core sections as discussed above can be difficult to use with sensitive imaging systems such as Magnetic Resonance Imaging (MRI) and the like because the metal content of the guidewire can create imaging artifacts that obscure the image produced, and can be heated or moved around by the strong MRI magnetic field. MRI compatible alloys or metals have lower magnetic susceptibilities. Such alloys include certain grades of stainless steel, Elgiloy and Nitinol. What has been needed is a guidewire that is compatible for use with sensitive imaging systems and methods such as MRI and the like.

SUMMARY

The invention is directed to an intracorporeal guiding device which can be in the form of a guidewire. The device includes an elongate member having a proximal section and a distal section. The distal section is made at least partially of a fiber composite matrix and has at least one segment with increasing flexibility in a distal direction. The fiber composite matrix can be configured to have little or no metal content so as to avoid creating imaging artifacts with sensitive imaging systems such as MRI and the like. In one embodiment, a flexible body is disposed about the distal section of the elongate member. The flexible body can have a variety of configurations, including a helical coil and a polymer layer. In a particular embodiment, the flexible body which consists of a polymer layer can be doped with a radiopaque material in order to improve visualization of the device under fluoroscopic imaging and the like.

In another embodiment, the elongate intracorporeal guiding device can have an elongate core disposed within a core lumen of the elongate member. The elongate core can be fixed or secured within the core lumen, or it may be moveable in an axial direction. Movement of the elongate core within the core lumen of the device may be used to adjust the flexibility of the distal section.

In another embodiment, a shapeable segment can be secured to the distal end of the elongate member with the flexible body disposed at least partially about the shapeable segment. In some embodiments, the shapeable segment is comprised of metal which can be flattened to provide improved shapeability in a specified orientation.

The invention is also directed to a method of making an elongate intracorporeal guiding device. The method includes disposing at least one layer of thin fiber about a mandrel. This can be done by winding, stranding, braiding or any other suitable method. A binding agent is then applied to the fiber material. If necessary, the binding agent can then be cured. Alternatively, a binding agent may be present on a thin fiber prior to disposing the thin fiber on the mandrel.

Furthermore, the invention is directed to a method of advancing an elongate intracorporeal guiding device within a patient's body. The method includes providing an elongate intracorporeal guiding device having a distal section configured so as not to create imaging artifacts when used with MRI imaging. The elongate intracorporeal guiding device is then inserted into the patient's body and advanced within the patient's body under MRI imaging to a desired site. A distal section configured to not create imaging artifacts with MRI imaging, or other sensitive imaging methods, can be a distal section constructed essentially of non-metallic fiber composite matrix optionally including polymer materials having little or not metallic content.

Finally, the invention is also directed to a dock exchange system for composite guidewires. The incorporation of a dock exchange system into a composite guidewire must consider the filament nature of the composite guidewire and how it is manufactured. The docking mechanism of the present invention is a hypotube or a crimped or crimpable tube attached to the proximal end of the guidewire which receives the tip of an extension guidewire. The hypotube or crimped or crimpable tube and the extension tip are so designed that once the latter is inserted, it is held in place unless a certain amount of tensile force is applied. The mechanism involves, for example, crimping the extension tip or placing magnets inside the hollow section.

BRIEF DESCRIPTION OF THE DRAWINGS

FIG. 1 is an elevational view in partial section of an intracorporeal guiding device having features of the invention.

FIG. 2 is a transverse cross sectional view of the intracorporeal guiding device of FIG. 1 taken along lines 2—2 in FIG. 1.

FIG. 3 is a transverse cross sectional view of the intracorporeal guiding device of FIG. 1 taken along lines 3—3 in FIG. 1.

FIG. 4 is a transverse cross sectional view of the intracorporeal guiding device of FIG. 1 taken along lines 4—4 in FIG. 1.

FIG. 5 is an elevational view in partial section of a part of a distal section of an intracorporeal guiding device having features of the invention.

FIG. 6 is a transverse cross sectional view of the intracorporeal guiding device of FIG. 5 taken along lines 6—6 in FIG. 5.

FIG. 15 shows a dock exchange system with a smaller inner diameter at the proximal end of the composite guidewire that constricts around the tip of the extension wire.

FIGS. 16–18 show a dock exchange system in which the filler material is a solid cylinder cut in half along its length to create a larger surface area to hold onto the tip of the extension wire.

FIG. 19 shows a dock exchange system in which the filler material has a texture that enhances the adhesion strength between the composite and extension guidewires.

FIGS. 20 & 21 show a dock exchange system in which the composite and extension guidewires are held together by magnetic force.

FIG. 22 shows a dock exchange system in which the hollow proximal section of the composite guidewire has a constriction for preventing the tip of the extension wire from sliding out.

DETAILED DESCRIPTION

Figure 7:
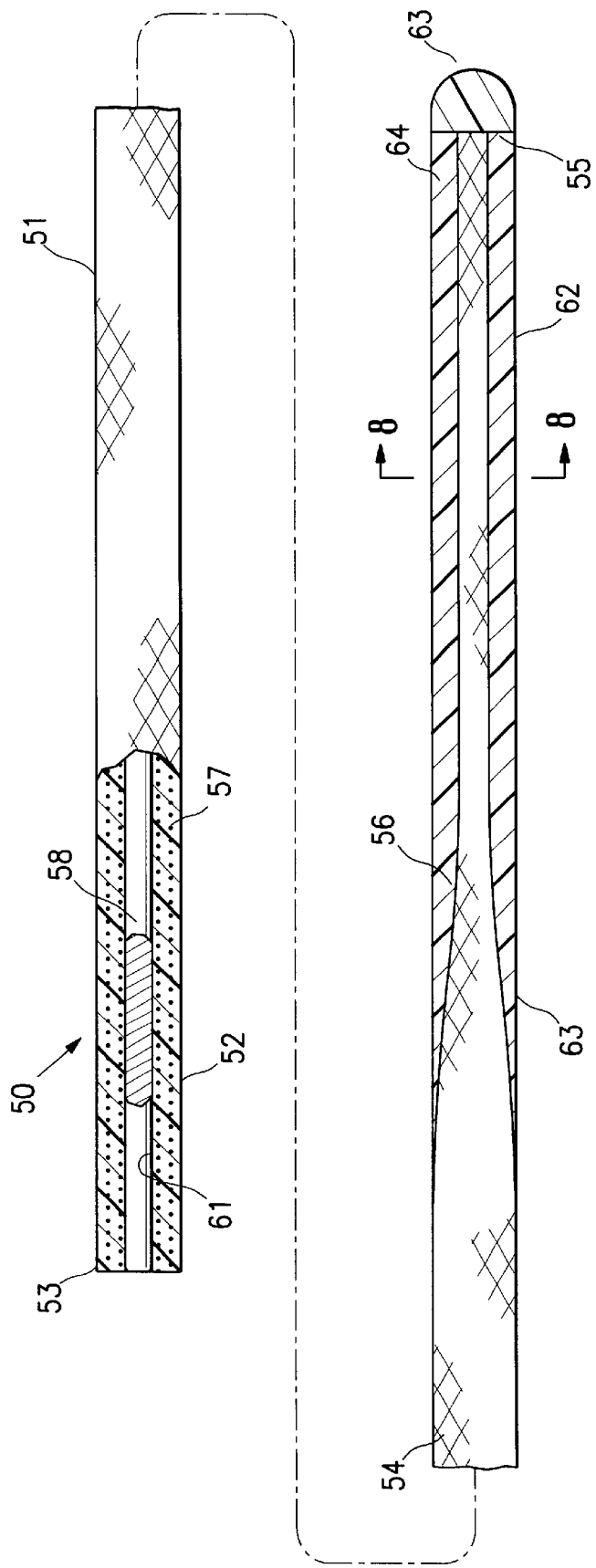
FIG. 7 is an elevational view in partial section of an intracorporeal guiding device having features of the invention.

FIG. 1 shows an intracorporeal guiding device 10 having features of the invention. An elongate member 11 made entirely of fiber composite matrix 12 has a proximal section 13, a proximal end 14, a distal section 15 and a distal end 16. Optionally, the elongate member 11 can be made partially out of fiber composite matrix 12. An optional core member 17 is disposed within a core lumen 18 of the elongate member 11 and is axially moveable within the core lumen 18 as indicated by arrow 21. The core member 17 has a proximal end 22 and a distal end 23 and may also be secured within the core lumen 18 either by frictional force, an epoxy or other adhesive, or by any other suitable means. An optional shapeable segment 24 having a proximal end 25 and a distal end 26 has an end cap 27 disposed at the proximal end 25 of the shapeable segment 24. The end cap 27 is disposed over and secured to the distal end 16 of the elongate member 11. The end cap 27 may be secured to the distal end 16 of the elongate member 11 by a friction fit, adhesive such as an epoxy, or any other suitable method. A flexible body in the form of a helical coil 30 having a proximal end 31 and a distal end 32 is disposed about the shapeable segment 24. The distal end 32 of the helical coil 30 is secured to the distal end 26 of the shapeable segment 24 with a body of solder 33 or the like. The proximal end 31 of the helical coil 30 can be similarly secured to the proximal end 25 of the shapeable segment 24.

The fiber composite matrix 12 of the elongate member 11 may be formed in a variety of configurations and from a variety of materials. In the embodiment the intracorporeal guiding device 10 of FIG. 1, the fiber composite matrix 12 can be formed from a plurality of non-metallic thin fibers 34 made of carbon fiber braided over a mandrel (not shown) in one or more layers. A cured or hardened binding agent 35 such as an epoxy resin, polyester resin or other suitable material is disposed about the thin fibers 34 to form the fiber composite matrix 12. The binding agent 35 can optionally be doped with a radiopaque material in order to provide radiopacity to the elongate member 11. Materials such as gold, platinum, platinum-iridium, tungsten, barium compounds or bismuth compounds may be used for doping the binding agent 35. In addition, one or more radiopaque thin fibers 34 can be made of the same or similar radiopaque materials discussed above with regard to radiopaque dopants for the binding agent and may be used when forming the fiber composite matrix 12 in order to provide radiopacity to the device 10. In addition, a conductor, insulated or uninsulated, or other type of conduit capable of carrying an electric, light, or other type of signal can be substituted or molded into the thin fibers 34. This can be done in order to carry a signal conveying information such as temperature or pressure from the distal end 16 to the proximal end 14 of the elongate member 11. If a fiber optic is used, light or a light signal can be transmitted from the distal end 16 to the proximal end 14 of the elongate member 11, or from the proximal end 14 to the distal end 16. During formation of the elongate member 11, the aforementioned mandrel is removed after the binding agent is cured.

During the formation process for the elongate member 11, the core member 17 could serve as a forming mandrel such as that discussed above, or a separate mandrel could be used for forming the fiber composite matrix 12 and then be removed. A core member 17 could then be inserted into the core lumen 18 once the forming mandrel is removed. The thin fiber 34 could also be wound or stranded about the forming mandrel prior to curing of the binding agent. Any appropriate number of layers of thin fiber 34 may be braided, stranded or wound about a forming mandrel in order to achieve a desired thickness of the fiber composite matrix 12. For an intracorporeal guiding member 10 having a elongate member 11 with a proximal section 13 having an outer diameter of about 0.008 to about 0.040 inches (about 0.020 to 0.102 cm), approximately 1 to about 10 layers of thin fiber 34 may be used, specifically, about 2 to about 6 layers of thin fiber. The thin fibers 34 can have a transverse dimension of about 0.0005 to about 0.002 inch (about 0.0013 to 0.0051 cm), specifically about 0.001 to about 0.0015 inch (about 0.0025 to 0.0038 cm) and can be made of carbon fiber. Other materials that can be used for the thin fibers 34 are polymeric substances such as Nylon (polyamides), Kevlar (polyarylamides), fiberglass and the like.

The flexibility of the elongate member 11 can be controlled to some degree by varying the manner in which the one or more thin fibers are configured within the fiber composite matrix with respect to axial position along the elongate member 11. Specifically, the angle the thin fiber 34 makes with a line parallel to a longitudinal axis 36 of the elongate member 12 adjacent the thin fiber 34 can affect the longitudinal flexibility of the elongate member and hence the intracorporeal guiding device 10. In addition, the distal section 15 of the elongate member 11 can be tapered to a reduced outer transverse dimension distally in one or more segments in order to increase the flexibility of such a segment. The tapering of a segment can be achieved by grinding a segment of substantially constant outer diameter after formation of the elongate member 11. Alternatively, the tapering of a segment could be achieved by varying the number of layers or configuration of the thin fiber or fibers 34 in the formation process of the elongate member 11. Also, the diameter of the core lumen 18 within the elongate member 11 could be increased distally in a segment of the distal section 15 of the elongate member 11 in order to increase the flexibility of the segment.

The core member 17 can be made from a metal such as stainless steel, MP35N, L605 or other high strength materials. The core member 17 may also be configured to be radiopaque and can have materials such as gold, platinum, platinum-iridium, tungsten and the like contained therein. The core member 17 may also be made of a fiber composite material similar to that of the elongate member 11 with a binding agent for such a fiber composite material being doped with a non-metallic radiopaque material in order to provide radiopacity to the core member 17 and avoid introduction of metallic content which might interfere with sensitive imaging methods as discussed above. The core member 17 can have an outer transverse dimension of about 0.001 to about 0.015 inches (about 0.0025 to 0.038 cm), specifically about 0.002 to about 0.005 inches (about 0.0051 to 0.0127 cm). The core member 17 can also be ground to have one or more tapered segments, specifically, tapered segment tapering distally to a reduced transverse dimension in order to provide greater flexibility in the distal section 15 of the elongate member 11.

Generally, the shapeable segment 24 can have a configuration similar to shapeable segments of guiding devices known in the art. Regarding the embodiment of the guiding device 10 shown in FIG. 1, the shapeable segment 24 is formed of stainless steel which has optionally been flattened. Specifically, the shapeable segment 24 has been flattened to a progressively greater degree in a distal direction. Thus, a thickness of the flattened portion at the proximal end 25 of the shapeable segment 24 is thicker than the thickness of the flattened portion of the shapeable segment 24 at the distal end 26 of the shapeable segment 24. The length of the flexible segment 24 can be from about 2 to about 30 cm, specifically, about 3 to about 10 cm. The thickness of the shapeable segment 24 at the flattened distal end can be from about 0.0005 to about 0.006 inch (about 0.0013 to 0.0152 cm), specifically, about 0.001 to about 0.002 inch (about 0.0025 to 0.0051 cm). Other materials suitable for the shapeable segment 24 include MP35N, L605 or other high strength materials.

The helical coil 30 can be made from a variety of suitable materials including stainless steel, platinum, platinum iridium, gold or the like. The helical coil 30 could also be made from a fiber composite matrix or other non-metal material in order to enable the intracorporeal guiding device 10 to have a distal section or an overall composition with a zero or minimum amount of metallic composition. As mentioned above, for certain applications and uses, minimizing the metallic content of the intracorporeal guiding device 10 improves compatibility with sensitive imaging devices such as MRI. The material of the helical coil 30 can have a transverse dimension of about 0.001 to about 0.005 inch (about 0.0025 to 0.0127 cm), specifically, about 0.002 to about 0.003 inch (about 0.0051 to 0.0076 cm).

The nominal outer transverse dimension of the proximal section 13 of the elongate member 11 can be from about 0.005 to about 0.035 inch (about 0.0127 to 0.0889 cm), specifically, about 0.01 to about 0.02 inch (about 0.0254 to 0.0508 cm), and more specifically about 0.012 to about 0.016 inch (about 0.0305 to 0.0407 cm). The overall length of the intracorporeal guiding device 10 can be from about 100 to about 300 cm, specifically about 150 to about 200 cm.

FIG. 2 is a transverse cross sectional view of the intracorporeal guiding device 10 of FIG. 1 taken along lines 2—2 in FIG. 1. The fiber composite matrix 12 is substantially concentrically disposed about the core member 17 as discussed above. In FIG. 3, the end cap 27 is disposed about the fiber composite matrix 12 which is substantially concentrically disposed about the core lumen 18. In FIG. 4, the helical coil 30 is disposed about the shapeable segment 24.

FIGS. 5 and 6 depict an alternative embodiment of a shapeable segment 40 wherein the end cap 27 of the shapeable segment 24 of FIG. 1 has been replaced with a handle portion 41 which is disposed within and secured to the distal end 42 of the elongate member 43. A configuration such as that shown in FIG. 5 allows for a smooth continuous transition from an outer surface 44 of the elongate member 43 to an outer surface 45 of the helical coil 46. A fiber composite matrix 47 is substantially concentrically disposed about the handle portion 41 of the shapeable segment 40. Components of the embodiment of the intracorporeal guiding device 48 shown in FIGS. 5 and 6 could have similar relationships, dimensions and materials to similar components of the embodiment of the intracorporeal guiding device 10 shown in FIGS. 1–4.

Figure 8:
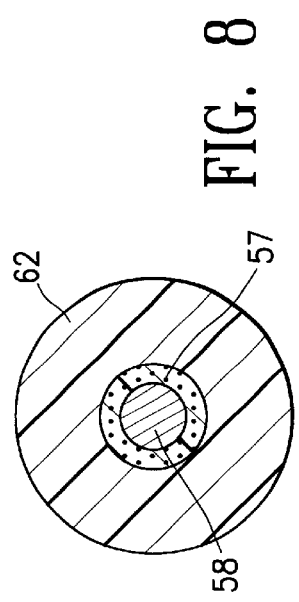
FIG. 8 is a transverse cross sectional view of the intracorporeal guiding device of FIG. 7 taken along lines 8—8 in FIG. 7.

FIGS. 7 and 8 show another embodiment of an intracorporeal guiding device 50 having features of the invention. An elongate member 51 has a proximal section 52, a proximal end 53, a distal section 54 and a distal end 55. The distal section 54 has a tapered segment 56 which tapers distally to a reduced transverse dimension in order to increase the flexibility of the distal section 54. The elongate member 51 is formed of a fiber composite matrix 57 such as that described above with regard to other embodiments of the invention. A core member 58 is optionally secured within a core lumen 61 of the elongate member 51. The core member 58 can be made of a non-metallic fiber composite matrix or other essentially non-metallic material in order to avoid interference with sensitive imaging systems such as MRI and the like. The tapered segment 56 of the distal section 54 of the elongate member 51 tapers in a curved configuration which can provide a smooth transition in flexibility. A flexible body in the form of a polymer layer 62 is substantially concentrically disposed about the distal section 54 of the elongate member 51. A rounded polymer cap 63 is secured to the distal end 55 of the elongate member 51 to facilitate securement of the polymer layer 62 to the elongate member 51 and to provide a rounded non-traumatic tip for the intracorporeal guiding device 50. The rounded polymer cap 63 can be a separate element as shown in FIG. 7, or it may be a continuation and integral portion of polymer layer 62. The polymer layer 62 has a proximal end 63 and distal end 64.

The polymer layer 62 can be made from a diverse range of materials, including polyurethane, polyethylene, Nylon, silicone, or any other suitable polymer. The polymer layer 62 can optionally be doped with a radiopaque material in order to facilitate imaging of the guiding device 50 under fluoroscopy. The polymer layer 62 can be applied by coextrusion, heat shrink, bonding with a suitable adhesive or any other appropriate method. The polymer layer 62 can be formed on the distal section 54 of the elongate member 51 or may be extruded independently and later secured to the distal section 54. The length and outer dimensions of the polymer layer 62 can be similar to those of the helical coil 30 discussed above. FIG. 8 is a transverse cross sectional view of the intracorporeal guiding device 50 of FIG. 7 taken along lines 8—8 in FIG. 7. The polymer layer 62 is shown substantially concentrically disposed about the fiber composite matrix 57 which is substantially concentrically disposed about the core member 58. Components of the embodiment of the intracorporeal guiding device 50 shown in FIGS. 7 and 8 could have similar relationships, dimensions and materials to similar components of the embodiment of the intracorporeal guiding device 10 shown in FIGS. 1–6.

Figure 9:
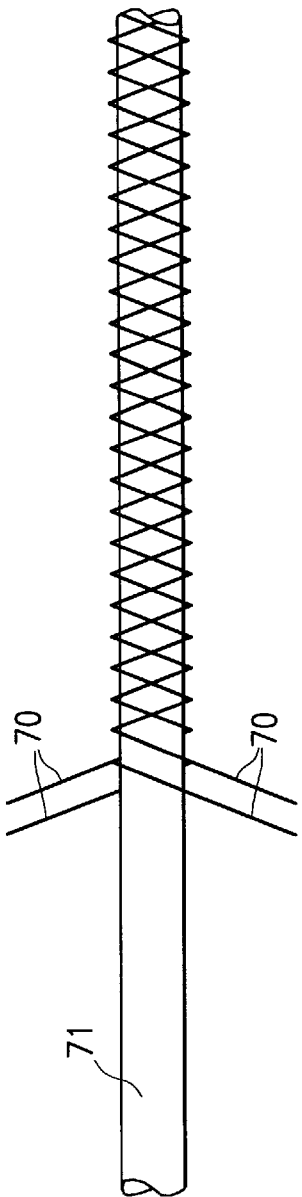
FIG. 9 is a schematic view of thin fibers being braided onto a mandrel.
Figure 10:
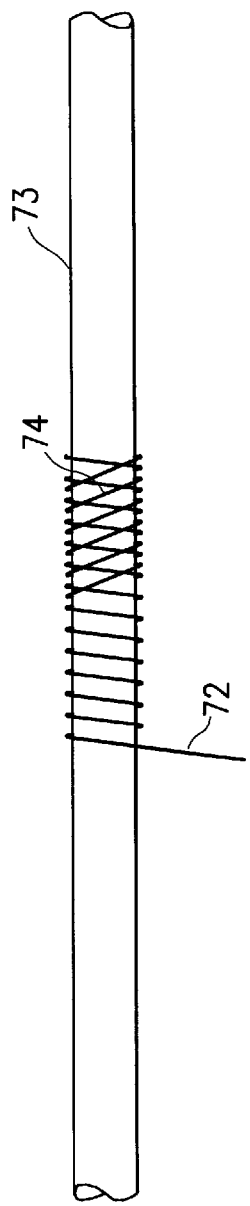
FIG. 10 is a schematic view of a thin fiber being wound onto a mandrel.
Figure 11:
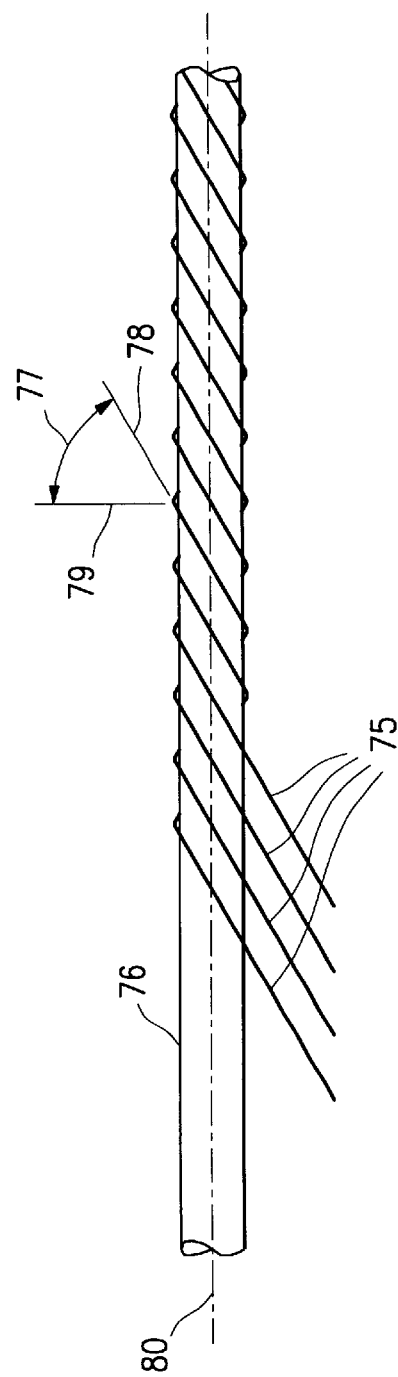
FIG. 11 is a schematic view of thin fibers being stranded onto a mandrel.

FIG. 9 illustrates four thin fibers 70 being braided onto a mandrel. FIG. 10 illustrates a single thin fiber 72 being wound onto a mandrel 73. A double layer section 74 is shown where the thin fiber 72 been wound back onto itself in order to form two layers. FIG. 11 shows four thin fibers 75 being stranded onto a mandrel 76. Also shown is the pitch angle 77 that a line 78 extending from one of the thin fibers 75 makes with a line 79 orthogonal to a longitudinal axis 80 of the mandrel 76. The pitch angle 77 of stranded, braided or wound thin fiber 75 can vary significantly. The pitch angle 77 can be just over zero degrees for a single thin fiber 75 being wound close spaced so that adjacent windings are touching each other. The pitch angle 77 can be up to 90 degrees for multiple stranded thin fibers 75 which extend essentially parallel to the longitudinal axis 80 of the mandrel 76. In one embodiment, the pitch angle 77 can be from about 20 to about 70 degrees, specifically, about 30 to about 60 degrees, and more specifically about 40 to about 50 degrees. Such variations in pitch angle 77 can be used to control the flexibility of the resulting elongate member for a fixed cross section of fiber composite material.

Figure 12:
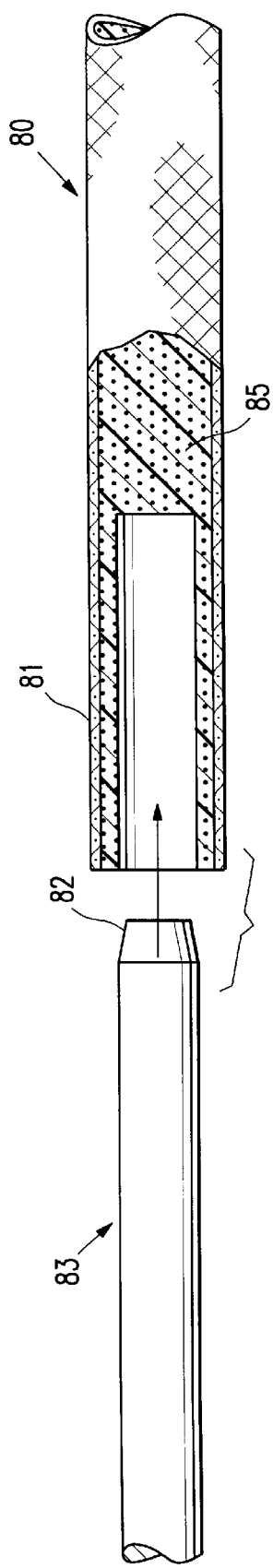
FIG. 12 shows a dock exchange system in which the composite guidewire has a hollow proximal end for receiving the distal end of the extension wire.
Figure 13:
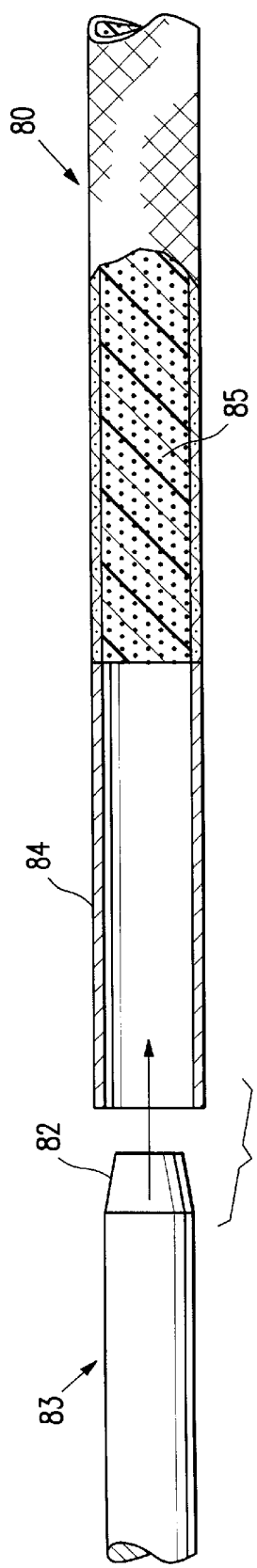
FIGS. 13 and 14 show alternative designs having a hypotube with an outer diameter identical to or smaller than the outer diameter of the proximal section of the composite guidewire.
Figure 14:
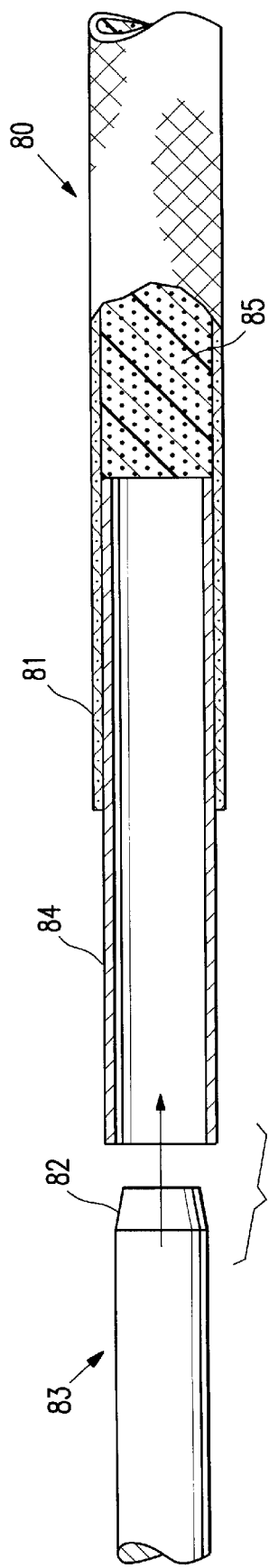

FIGS. 12–22 illustrate dock exchange systems of the present invention for composite guidewires. FIG. 12 shows a dock exchange system in which the composite guidewire 80 has a hollow proximal end 81 for receiving the distal end 82 of the extension wire 83. FIGS. 13 and 14 show alternative designs having a hypotube or a crimped or crimpable tube 84. The outer diameter of the hypotube or the crimped or crimpable tube is either identical to (FIG. 13) or smaller than that of the proximal section of the composite guidewire (FIG. 14).

The hypotube or crimped or crimpable tube may be made of a metal (such as steel), an alloy (such as Nitinol) or a polymer (such as a polyetheretherketone). The tube is from about 1 cm to about 3 cm in length. The wall of the tube is from about 0.0002 inches to about 0.003 inches in thickness.

If the composite filaments are wound around a continuous spool of mandrel that is removed after winding and cutting to length, then the hollow section is naturally made at the proximal end. If a hypotube or crimped or crimpable tube is desired, these can be added after the mandrel is removed. They can be inserted into the hollow left by the mandrel, or can be attached to the end of the composite guidewire using glue, thermal bonding, mechanical bonding or the combination thereof.

If the composite filaments are wound around a precut length of the mandrel that is removed after the winding process, then the hollow section is also naturally made at the proximal end. In this construction, if a hypotube or crimped or crimpable tube is desired, these can be temporarily attached to the end of the mandrel before the winding process and left in place when the mandrel is removed. Alternatively, they can also be inserted into the hollow left by the mandrel, or can be attached to the end of the composite guidewire using glue, thermal bonding, mechanical bonding or the combination thereof.

If the composite filaments are wound around a continuous spool of mandrel that becomes a permanent part of the guidewire, then the hollow section is created by drilling into the proximal end of the mandrel after the composite wire has been cut to length. If a hypotube or crimped or crimpable tube is desired, these can be attached after winding and cutting to length to the end of the composite guidewire using glue, thermal bonding, mechanical bonding or the combination thereof.

If the composite filaments are wound around a precut length of the mandrel that becomes a permanent part of the guidewire, then the hollow section is created by just winding past the end of the mandrel. If a hypotube or crimped or crimpable tube is desired, these can be attached either permanently to the proximal end of the mandrel before the winding process or afterwards in a similar fashion as stated above.

The hollow proximal section of the composite guidewire or the hypotube may be partially or totally filled with a filler material to enhance the attachment strength between the composite guidewire and the extension guidewire. With a hollow proximal section, the filler material may be incorporated during the braiding or winding process to make the composite guidewire. In other words, the composite wires are wound around the filler material. With a hypotube or crimped or crimpable tube, the filler material may be added before or after the braiding or winding process to make the composite guidewire.

The filler material may be certain grades of silicone, textured polymer, adhesive materials, magnets or a combination of two or more thereof.

When the distal end of the extension guidewire is inserted into or in contact with the filler material it remains attached due to the interfacial adhesion or magnetic attraction force between the filler material and the tip of the extension guidewire.

The filler material 85 may be tubular in form 86 with a small inner diameter 87 that constricts around the tip of the extension wire as shown in FIG. 15. In addition to being tubular, the filler polymer may have a constricted end, which prevents the tip of the extension guidewire from easily sliding out once it is inserted. The filler material may also be a solid cylinder cut in half along its length 88 which creates a larger surface area to hold onto the tip 82 of the extension guidewire 83 as shown in FIGS. 16–18. The filler material may also be a piece of solid, which the tip of the extension guidewire may puncture into.

FIG. 19 shows that when the filler material 85 is a textured polymer, such as can be imparted by a molding or extrusion process or the proper selection of polymer blends, the surface of the filler material that comes in contact with the tip 82 of the extension guidewire 83 may have a texture that enhances the adhesion strength between the composite and extension guidewires. When the filler material is an adhesive material, such as some classes of silicones or acrylates, the filler material may be an adhesive glue that is designed to strongly hold on the tip of the extension guidewire yet still allow repeated attachment and detachment of the tip.

The proximal section of the composite guidewire may instead have one or several magnets that are incorporated before, during or after the winding process. In the design as shown in FIG. 20, the magnet(s) 89 are cylindrical and embedded at the bottom closed end of the hollow section. When the tip of the extension guidewire is inserted into the hollow section, hypotube, crimped or crimpable tube, it is held in place due to its attraction to the magnets. The tip of the extension guidewire may also be fitted with magnets 90 that are aligned to enhance the attractive force to the magnets. FIG. 21 shows that the magnet or magnets inside the composite guidewire may instead form a half cylinder 91 that sets inside the hollow section, hypotube, or crimped or crimpable tube. The tip of the extension guidewire may be shaped as a half-cylinder or have a correctly aligned half-cylinder magnet 92 as well. This tip can then slide into the proximal end of the composite guidewire and due to the attraction of the two magnets or the magnet to the metal, it stays in place.

Alternatively, the hollow proximal section, hypotube, or the crimped or crimpable tube may have a constriction or constrictions 93 along its length that prevent the tip of the extension guidewire from readily sliding out once inserted, as shown in FIG. 22.

In order to enhance dockability, the tip of the extension guidewire may have one or more of the following characteristics. The tip of extension guidewire may be made of a metal, an alloy or a polymer, as those described above for the hypotube and crimped or crimplable tube. The tip of the extension guidewire may be uncoated or coated with a tacky material such as certain grades of silicon, textured polymers or adhesives to enhance the adhesion strength. The extension guidewire may be round, flat or oblong along its length and it may be nontapered or tapered with one or more dimensions increasing or decreasing as one moves distally along its length. The tip of the extension guidewire may be formed with a ball, flared or expanded end. Furthermore, the tip of the extension guidewire may have a magnet or magnets as described above.

In another embodiment, the end of the composite guidewire may be fitted with the tip as described above. In other words, the extension guidewire now has the docking station. In this case, the tip or tips are attached either before, during or after the winding process to make the composite guidewire. The tip may instead be a modification to the proximal end of the mandrel if the mandrel is to become a permanent part of the composite guidewire. The modification may be done before or after the winding process to make the composite guidewire.

While particular forms of the invention have been illustrated and described, it will be apparent that various modifications can be made without departing from the spirit and scope of the invention. Accordingly, it is not intended that the invention be limited, except as by the appended claims.

What is claimed is:

1. An intracorporeal composite guidewire comprising:
   an extension guidewire; and
   a proximal section which is hollow or is attached to a hypotube or is a crimped or crimpable tube to receive the extension guidewire;
   wherein the extension guidewire has a half-cylinder magnetic tip aligned to enhance attraction to magnets in the hollow proximal section of the composite guidewire, the hypotube or the crimped or crimpable tube.

2. The intracorporeal composite guidewire of claim 1 wherein the hypotube or the crimped or crimpable tube is made of a metal, an alloy or a polymer.

3. The intracorporeal composite guidewire of claim 1 wherein said hypotube or crimped or crimpable tube is attached to the proximal section of said composite guidewire using glue, thermal bonding, mechanical bonding or the combination thereof.

4. The intracorporeal composite guidewire of claim 1 wherein said hollow proximal section of the composite guidewire, the hypotube or the crimped or crimpable tube attached to the proximal section of the composite guidewire is partially or totally filled with a filler material.

5. The intracorporeal composite guidewire of claim 4 wherein said filler material is selected from a group consisting of certain grades of silicone, textured polymers, adhesive materials and magnets.

6. The intracorporeal composite guidewire of claim 5 wherein the hollow proximal section of the composite guidewire has at least one magnet.

7. The intracorporeal composite guidewire of claim 6 wherein the magnet includes a tip having a semi-circular cross-section.

8. The intracorporeal composite guidewire of claim 6 wherein the magnet(s) is embedded at the bottom closed end of the hollow proximal section.

9. The intracorporeal composite guidewire of claim 1 wherein the hollow proximal section, the hypotube or the crimped or crimpable tube has a constriction or constrictions along its length to prevent the tip of the extension guidewire from sliding out once inserted.

10. The intracorporeal composite guidewire of claim 1 wherein the tip of the extension guidewire is made of a metal, an alloy or a polymer.

11. The intracorporeal composite guidewire of claim 1 wherein the tip of the extension guidewire is coated or uncoated.

12. The intracorporeal composite guidewire of claim 1 wherein the extension guidewire is round, flat or oblong along its length.

13. The intracorporeal composite guidewire of claim 1 wherein the extension guidewire is untapered or tapered with one or more dimensions increasing or decreasing as one moves distally along its length.

14. An intracorporeal composite guidewire comprising:
   a proximal section which is hollow or is attached to a hypotube or is a crimped or crimpable tube to receive an extension guidewire; and
   a magnet inside the hollow proximal section of the composite guidewire, the hypotube or the crimped or crimpable tube, wherein the magnet forms a half cylinder and is configured to receive a tip of the extension guidewire which is shaped as a half-cylinder or has a half-cylinder magnet.

* * * * *

UNITED STATES PATENT AND TRADEMARK OFFICE
CERTIFICATE OF CORRECTION

PATENT NO. : 6,451,026 B1  Page 1 of 1
DATED : September 17, 2002
INVENTOR(S) : Emmanuel C. Biagtan et al.

It is certified that error appears in the above-identified patent and that said Letters Patent is hereby corrected as shown below:

<u>Title page,</u>
Item [75], Inventors, last two lines, change "San Luis Obispo", to read -- Temecula --.

Signed and Sealed this

Twenty-eighth Day of January, 2003

JAMES E. ROGAN
*Director of the United States Patent and Trademark Office*